United States Patent [19]

Kameswaran

[11] Patent Number: 5,750,726
[45] Date of Patent: May 12, 1998

[54] PROCESS FOR THE MANUFACTURE OF 2-ARYL-5-PERFLUOROALKYLPYRROLE DERIVATIVES AND INTERMEDIATES USEFUL THEREFOR

[75] Inventor: Venkataraman Kameswaran, Princeton Junction, N.J.

[73] Assignee: American Cyanamid Company, Madison, N.J.

[21] Appl. No.: 883,768

[22] Filed: Jun. 27, 1997

Related U.S. Application Data

[60] Provisional application No. 60/020,759 Jun. 28, 1996.

[51] Int. Cl.$^6$ .................... C07D 207/34; C07D 255/40
[52] U.S. Cl. .................... 548/561; 548/560; 548/562; 549/76; 549/493; 558/404
[58] Field of Search .................... 549/76, 493; 548/561, 548/562, 560; 558/404

[56] References Cited

U.S. PATENT DOCUMENTS

| | | | |
|---|---|---|---|
| 3,290,326 | 12/1966 | Hoffer et al. | 260/307 |
| 4,150,143 | 4/1979 | Nevile et al. | 424/272 |
| 4,632,930 | 12/1986 | Carini et al. | 514/365 |
| 5,010,098 | 4/1991 | Brown et al. | 514/426 |
| 5,030,735 | 7/1991 | Addor et al. | 548/531 |
| 5,145,986 | 9/1992 | Kameswaran | 548/531 |
| 5,380,738 | 1/1995 | Norman et al. | 514/374 |
| 5,426,225 | 6/1995 | Kameswaran | 564/212 |
| 5,446,170 | 8/1995 | Kameswaran | 548/517 |
| 5,449,789 | 9/1995 | Kameswaran | 548/561 |
| 5,574,175 | 11/1996 | Kameswaran | 548/517 |
| 5,631,379 | 5/1997 | Kameswaran | 548/233 |

OTHER PUBLICATIONS

McEwen, et al., *Synthetic Uses of Open–Chain Analogues of Reissert Compounds*, Journal of Organic Chemistry, 1980, 45, pp. 1301–1308.

McEwen, et al., *1,3–Dipolar Addition Reactions of Reissert Compounds*, Journal of the American Chemical Society, 1971, 93:18, pp. 4479–4484.

*Primary Examiner*—Joseph McKane
*Attorney, Agent, or Firm*—John W. Hogan, Jr.

[57] ABSTRACT

There is provided a single step procedure to prepare 2-aryl-5-perfluoroalkylpyrrole derivatives directly from the perfluoroacetylated Strecker reaction product. Said pyrrole derivatives are insecticidal and also useful as precursors to other insecticidal arylpyrrole compounds.

Further provided are amide nitrile intermediates, useful in the preparation of insecticidal arylpyrrole compounds.

11 Claims, No Drawings

PROCESS FOR THE MANUFACTURE OF 2-ARYL-5-PERFLUOROALKYLPYRROLE DERIVATIVES AND INTERMEDIATES USEFUL THEREFOR

This application is based on Provisional Application No. 60/020,759 filed Jun. 28, 1996.

BACKGROUND OF THE INVENTION

Arylpyrrole carbonitrile compounds are highly effective insecticidal, acaricidal and nematocidal agents with a unique mode of action and a broad spectrum of activity. In particular, 2-aryl-5-(trifluoromethyl)pyrrole-3-carbonitrile compounds demonstrate effective control across a wide array of pests and can control resistant pests such as pyrethroid-, organophosphate-, cyclodiene-, organochlorine-, organotin-, carbamate-, and benzophenyl-urea-resistant biotypes of Helicoverpa/Heliothis spp., Spodoptera spp., Trichoplusia spp., Pseudoplusia spp. and Tetranychus spp. Because there is no apparent cross-resistance, 2-aryl-5-(trifluoromethyl)pyrrole-3-carbonitrile compounds and their derivatives have potential for use in resistance management programs. Further, said pyrroles have little effect on beneficial species making them excellent candidates for integrated pest management programs, as well. These programs are essential in today's crop production.

Therefore, methods to prepare said pyrroles and intermediates to facilitate their manufacture are of great use. Among the present methods to prepare 2-aryl-5-(trifluoromethyl)pyrrole-3-carbonitrile on a manufacturing scale are the 1,3-dipolar cycloaddition of 3-oxazolin-5-one with 2-chloroacrylonitrile (U.S. Pat. No. 5,030,735) and the cycloaddition reaction of the appropriate oxazole amine derivatives with 2-chloroacrylonitrile or 2,3-dichloropropionitrile (U.S. Pat. No. 5,446,170).

Also known is the 1,3-dipolar cycloaddition of the mesionic intermediate product of the acid catalyzed cyclization of a Reissert compound with a suitable alkyne to give an N-substituted pyrrole product as described by W. M. McEwen, et al. *Journal of Organic Chemistry*, 1980, 45, 1301–1308. However these mesionic intermediates undergo a 1,4 cycloaddition reaction with ethylenic dieneophiles to give an aroylpyrrole derivative and, as such, are not useful as insecticidal arylpyrrole precursors.

Therefore, it is an object of this invention to provide an alternate and efficient process of manufacture for the arylpyrrole class of highly effective pesticides.

It is a another object of this invention to provide a source of important intermediate amide nitrile compounds useful in the manufacture of arylpyrrole pesticidal agents.

It is an advantage of this invention that the manufacturing process consists of a single effective step which produces a formula I arylpyrrole precursor capable of being converted to a wide variety of highly effective insecticidal, acaricidal and nematocidal agents.

It is a further advantage of this invention that the overall number of synthetic steps from the initial Strecker reaction product to the final insecticidal arylpyrrole product is reduced from the number of synthetic steps required by employing current known methods such as those described hereinabove.

It is a feature of this invention that the process provides a regiospecific product. These and other features and objects of the invention will become more apparent from the detailed description set forth hereinbelow.

SUMMARY OF THE INVENTION

The present invention provides a single step effective process for the manufacture of a 2-aryl-5-perfluoroalkylpyrrole of formula I

wherein R is hydrogen or $C_1$–$C_6$alkyl optionally substituted with one $C_1$–$C_4$alkoxy or phenyl group;

n is an integer of 1, 2, 3, 4, 5, 6, 7 or 8;

W is CN, $NO_2$, $COOR_1$, or $COR_2$;

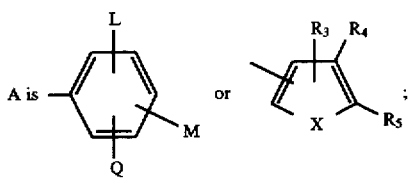

L is hydrogen or halogen;

M and Q are each independently hydrogen, halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$alkylsulfinyl or when M and Q are on adjacent positions they may be taken together with the carbon atoms to which they are attached to form a ring in which MQ represents the structure —$OCH_2O$—, —$OCF_2O$— or —CH=CH—CH=CH—;

$R_1$ and $R_2$ are each independently $C_1$–$C_4$alkyl;

$R_3$, $R_4$, and $R_5$ are each independently hydrogen, halogen, $NO_2$, CHO or $R_4$ and $R_5$ may be taken together with the atoms to which they are attached to form a ring in which $R_4R_5$ is represented by the structure

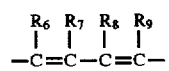

$R_6$, $R_7$, $R_8$ and $R_9$ are each independently hydrogen, halogen, CN or $NO_2$; and X is O or S which comprises reacting an amide nitrile of formula II

wherein A, R and n are as described hereinabove for formula I with at least one molar equivalent of a dieneophile of formula III

wherein W is as described hereinabove for formula I and Y is hydrogen, Br or Cl with the proviso that when R is hydrogen, then Y must be Br or Cl, in the presence of an acid and a solvent and essentially in the absence of consequences of water. To the extent water is present in the process of the invention, hydrolysis of the starting materials will take place resulting in lower yields and decreased purity of the desired arylpyrrole end product.

The term halogen as used in the specification and claims designates Cl, Br, F or I and the term haloalkyl embraces any alkyl group of $\chi$ carbon atoms which may contain from 1 to $2\chi+1$ halogen atoms which may be the same or different.

The present invention also provides an amide nitrile compound of formula IIa

wherein n and A are as described hereinabove for formula I and R' is $C_1$–$C_6$alkyl optionally substituted with one $C_1$–$C_4$alkoxy or phenyl group.

DETAILED DESCRIPTION OF THE INVENTION

Processes, to be useful on a manufacturing scale, preferentially contain key intermediate compounds which may be obtained in high to quantitative yield, which are stable either upon isolation or in situ, which may be produced from simple or readily available starting materials and which may be readily converted to the desired end-product of manufacture in a minimum of reaction steps, in optimum yield and purity and, if applicable, regio- or stereospecifically.

It has now been found that 2-aryl-5-perfluoroalkylpyrroles of formula I may be prepared directly from the perfluoroacylated amino nitrile product of formula II via a single step synthesis, by the reaction of the formula II compound with a dieneophile of formula III in the presence of an acid and a solvent and essentially in the absence of water. The reaction is shown in flow Diagram I wherein n, A, R and W are as defined hereinabove.

Solvents contemplated for use in the process of the invention are those solvents capable of sustaining essentially anhydrous conditions and partial or complete dissolution of the amide nitrile compound of formula II. Said solvents include organic solvents such as: aromatic hydrocarbons such as benzene, xylene, toluene and the like, preferably toluene; chlorinated aromatic hydrocarbons such as chlorobenzene; carboxylic acid amides such as dimethylformamide, N-methylpyrrolidone, and the like, preferably dimethylformamide; nitriles such as acetonitrile, propionitrile, and the like; alcohols such as isopropanol, t-butanol, sec-butanol, and the like, preferably t-butanol. These solvents may be used alone or in combination of two or more.

Acids suitable for use in the process of the invention are any acids capable of relative dehydration since increased water gives decreased yield or purity. Among the suitable acids are sulfuric acid, methanesulfonic acid, trifluoromethanesulfonic acid, p-toluenesulfonic acid, tetrafluoroboric acid, tetrafluoroboric acid complexes, and the like. Boron trifluoride complexes such as borontrifluoride acetic acid, boron trifluoride dihydrate, and the like are also suitable acids.

Preferred arylpyrrole compounds of formula I obtained by the process of the invention are those wherein n is 1 or 2, W is CN and A is optionally substituted phenyl. More preferred formula I compounds obtained by the inventive process are those wherein n is 1 or 2, W is CN, A is optionally substituted phenyl and R is hydrogen, methyl or ethoxymethyl; particularly preferred are those wherein n is 1, W is CN, A is p-chlorophenyl, 2,5-dichlorophenyl, 3,4,5-trichlorophenyl, p-bromophenyl, α,α,α-trifluoro-p-tolyl or p-trifluoromethoxyphenyl and R is hydrogen, methyl or ethoxymethyl.

The formula II amide nitrile compounds wherein R is hydrogen and their preparation are described in U.S. Pat. No. 5,426,225. Formula II amide nitrile compounds wherein R is other than hydrogen, i.e. formula IIa, may be obtained via the perfluoroacylation of the appropriate amino nitrile of formula VI. The formula VI aminonitriles are correspondingly readily obtained from their available benzaldehyde, furfurylaldehyde or thienylmethylaldehyde precursors via the well-known Strecker reaction. The reaction sequence is shown in Flow Diagram II wherein n, A and R are as described hereinabove for formula I, m is an integer of 1 or 2, $X_1$ is Cl, $OR_{10}$ or O and $R_{10}$ is hydrogen or $C_1$–$C_6$alkyl with the proviso that when $X_1$ is O, then m must be 2 and when $X_1$ is Cl or $OR_{10}$, then m must be 1.

Flow Diagram I

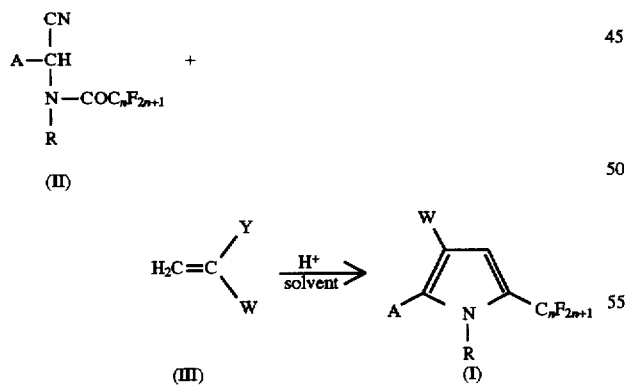

Flow Diagram II

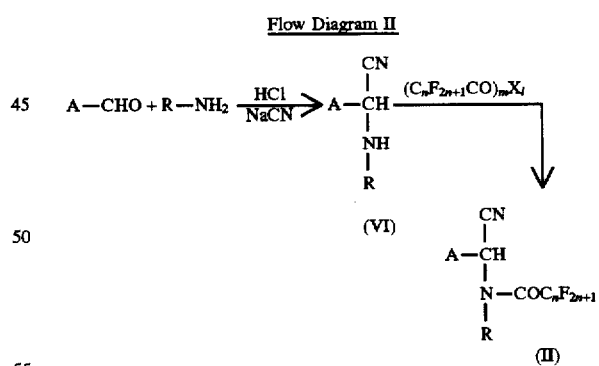

Advantageously, the amide nitrile of formula II may be converted directly to the desired 2-aryl-5-perfluoroalkylpyrrole of formula I in a single step as shown hereinabove in flow diagram I.

In accordance with the inventive process, the amide nitrile of formula II may be dispersed in a suitable solvent or solvent mixture and admixed with at least one molar equivalent of an appropriate dieneophile of formula III in the presence of an acid under essentially anhydrous reaction conditions. The thus-obtained formula I pyrrole may be isolated using conventional means such as extraction, filtration, distillation, chromatographic separation or the like. The rate of formation of the formula I pyrrole may be increased with increased temperature. However, it is understood that excessively high reaction temperatures may cause decomposition or undesired side reactions and a concomitant decrease in product yield and purity. Typical reaction temperatures may range from 20° C. to the reflux temperature of the solvent or solvent mixture. Typically, temperatures of about 20°–150° C. are employed, preferably 40°–100° C.

The present invention also provides amide nitrile intermediates of formula IIa

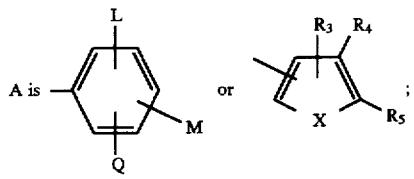

wherein n is an integer of 1, 2, 3, 4, 5, 6, 7 or 8;

R' is $C_1$–$C_6$alkyl optionally substituted with one $C_1$–$C_4$alkoxy or phenyl group;

L is hydrogen or halogen;

M and Q are each independently hydrogen, halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$alkylsulfinyl or when M and Q are on adjacent positions they may be taken together with the carbon atoms to which they are attached to form a ring in which MQ represents the structure —$OCH_2O$—, —$OCF_2O$— or —CH=CH—CH=CH—;

$R_1$ and $R_2$ are each independently $C_1$–$C_4$alkyl;

$R_3$, $R_4$, and $R_5$ are each independently hydrogen, halogen, $NO_2$, CHO or $R_4$ and $R_5$, may be taken together with the atoms to which they are attached to form a ring in which $R_4R_5$ is represented by the structure

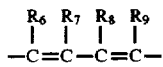

$R_6$, $R_7$, $R_8$ and $R_9$ are each independently hydrogen, halogen, CN or $NO_2$; and X is O or S.

Preferred formula IIa intermediate compounds of the invention are those wherein n is 1 or 2, R' is methyl or ethoxymethyl and A is optionally substituted phenyl.

More preferred compounds of formula IIa are those wherein n is 1, R' is methyl and A is p-chlorophenyl, p-bromophenyl, 3,5-dichlorophenyl, 3,4,5-trichlorophenyl, p-(α,α,α-trifluoro)tolyl or p-trifluoromethoxy phenyl.

While the formula I compounds have insecticidal activity, their greatest utility may be as precursors to certain formula IV compounds. Advantageously, the process of the invention allows the preparation of formula IV 2-aryl-4-halo-5-(perfluoroalkyl)pyrrole-3-carbonitrile insecticidal, acaricidal and nematocidal agents in as few as four synthetic steps from readily available arylaldehyde starting materials.

Thus, perfluoroacylation of the Strecker reaction product (VI) followed by the inventive process step gives the arylpyrrole precursor (I), which may be halogenated to give the desired pesticidal product (IV). The synthesis is illustrated in flow diagram III, wherein n, A, R, Y and W are as described hereinabove and Hal is halogen, preferably Br or Cl.

Flow Diagram III

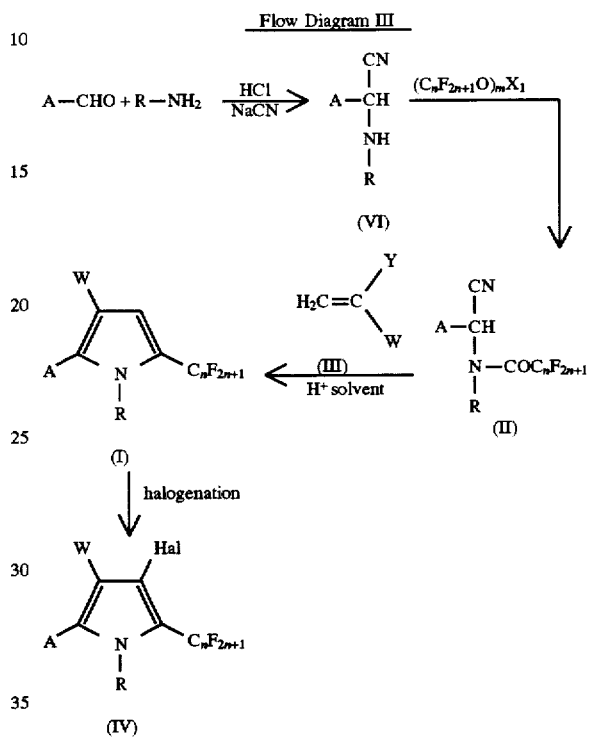

Halogenation methods may be any known methods such as those described in U.S. Pat. No. 5,010,098 or U.S. Pat. No. 5,449,789.

In order to provide a more clear understanding of the invention, the following examples are set forth below. These examples are merely illustrative and are not to be understood to limit the scope or underlying principles of the invention in any way. Indeed, various modifications of the invention, in addition to those shown and describe d herein, will become apparent to those skilled in the art from the following examples and the foregoing description. Such modifications are also intended to fall within the scope of the appended claims.

The terms $^1$H NMR, $^{13}$C NMR and $^{19}$F NMR designate proton, carbon 13 and fluorine 19 nuclear magnetic resonance, respectively. The term HPLC designates high performance liquid chromatography.

EXAMPLE 1

Preparation of N-Isopropylamino(p-chlorophenyl) acetonitrile

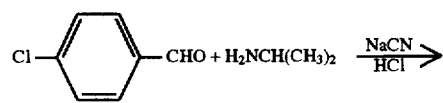

-continued

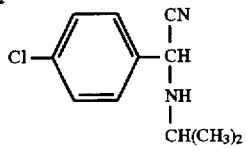

Isopropylamine (88.7 g, 1.5 mol) is added to an aqueous solution of concentrated hydrochloric acid (125 mL, 1.5 mL) in water at 25°–30° C. The resultant mixture is treated sequentially with a solution of sodium cyanide (53.9 g, 1.1 mol) in water and methylene chloride at 30° C., warmed to 35° C., treated with a solution of p-chlorobenzaldehyde (140.6 g, 1 mol) in methylene chloride over a 15–25 minute period, allowed to warm, held for 3 hours at 45° C. and cooled to room temperature. The phases are separated and the organic phase is washed with water and concentrated in vacuo to give a residue. The residue is crystallized from heptane to give the title product as a pale yellow crystalline solid, 190.3 g (91.2% yield), mp 72.0°–73.0° C., identified by $^1$H and $^{13}$C NMR analyses.

EXAMPLE 2

Preparation of N-(p-chloro-α-cyanobenzyl)-2,2,2-trifluoro-N-isopropylacetamide

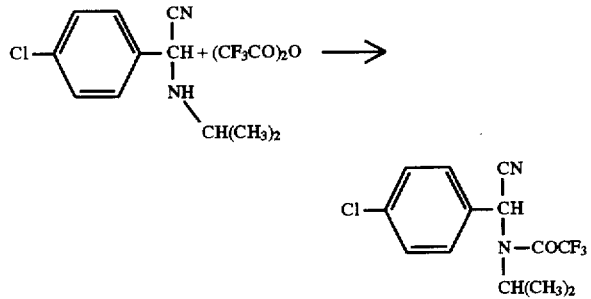

A slurry of N-isopropylamino(p-chlorophenyl)acetonitrile (25.0 g, 0.12 mol) in trifluoroacetic anhydride is gently heated at reflux temperature for 20 hours and concentrated in vacuo to give an oil residue. The oil is crystallized from toluene/heptane to give the title product as a white solid, 26.5 g (72.4% yield) mp 78.5°–79.5° C., identified by $^1$H, $^{13}$C and $^{19}$F NMR analyses.

EXAMPLE 3

Preparation of N-Benzyl-N-(p-chloro-α-cyanobenzyl)-2,2,2-trifluoroacetamide

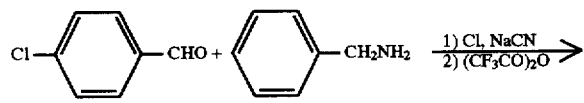

-continued

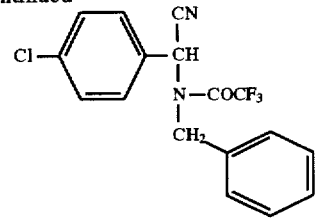

Aqueous hydrochloric acid (62.5 mL of 12N, 0.75 mol) in water (100 mL) is treated with benzylamine (80.4 g, 0.75 mol) at <20° C., then treated sequentially with a solution of sodium cyanide (27.0 g, 0.55 mol) in water and methylene chloride, warmed to 35° C., treated with a solution of p-chlorobenzaldehyde (70.3 g, 0.5 mol) in methylene chloride, allowed to warm to 50° C., and held at 45° C. for 3.5 hours. The phases are separated and the organic phase is washed with water and concentrated to a syrup residue. The residue is dissolved in toluene and ethyl acetate, treated with trifluoroacetic anhydride (105.0 g, 0.5 mol) at 20°–30° C. over a 30 minute period and diluted with heptane. The resultant white fluffy solid precipitate is filtered and dried to give the title product, 119.8 g (70.7% yield), mp 131°–132° C., identified by $^1$H, $^{13}$C and $^{19}$F NMR analyses.

EXAMPLE 4

Preparation of 2-(p-Chlorophenyl)-5-(trifluoromethyl)-pyrrole-3-carbonitrile

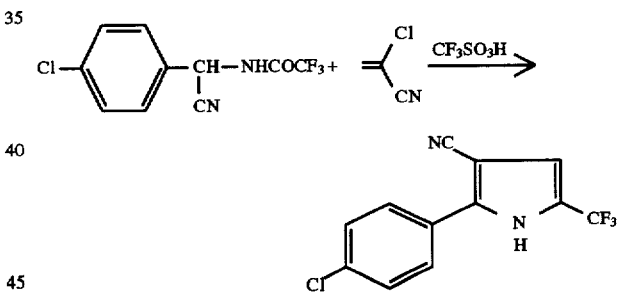

A mixture of N-(p-chloro-α-cyanobenzyl)-2,2,2-trifluoroacetamide (10.5 g, 0.04 mol) and toluene is cooled to 5°–10° C. under a nitrogen atmosphere, treated with trifluoromethanesulfonic acid (12.0 g, 0.08 mol) over a 20 minute period, allowed to warm to room temperature and held at 25° C. for 3 hours. The formation of the intermediate 5-amino oxazole salt is monitored by $^{19}$F NMR (DMSO-$d_6$). When the intermediate salt formation is complete, the mixture is cooled below 20° C., treated with dimethylformamide and 2-chloroacrylonitrile (5.25 g, 0.06 mol), held at 25° C. for 16–18 hours, and treated with ethyl acetate and water. The phases are separated and the organic phase is washed with water and concentrated in vacuo to give a solid residue. Flash column chromatography of the residue on silica gel, packed and eluted respectively with 15% and 20% ethyl acetate in heptane gives the title product as pale yellow crystals, 6.14 g (57% yield), mp 237°–240° C., identified by HPLC and NMR analyses.

EXAMPLE 5

Preparation of 2-Aryl-5-(trifluoromethyl)pyrrole derivatives

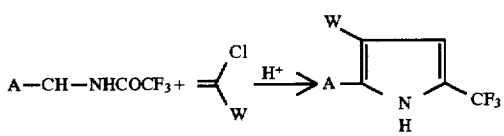

Using essentially the same procedure described in Example 4 and substituting the appropriate trifluoroacetylated amino nitrile starting material, the following products are obtained:

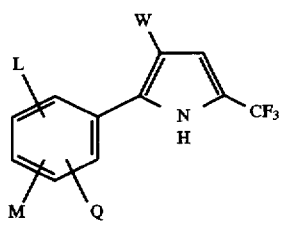

| W | L | M | O | mp °C. | % yield |
|---|---|---|---|---|---|
| CN | 3-Cl | 4-Cl | H | 241–244 | 55 |
| CN | H | 4-Br | H | 249–251 | 35 |

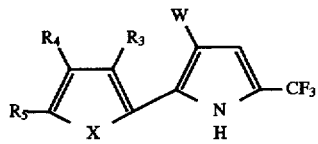

| W | X | $R_3$ | $R_4$ | $R_5$ | mp °C. | % yield |
|---|---|---|---|---|---|---|
| CN | S | H | H | H | | |

EXAMPLE 6

Preparation of 2-(p-Chlorophenyl)-5-trifluoromethyl)-pyrrole-3-carbonitrile

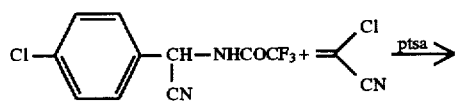

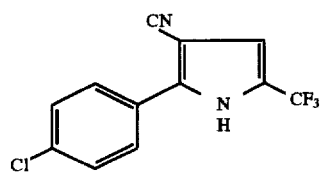

A mixture of p-toluenesulfonic acid (ptsa), monohydrate (19.1 g, 0.1 mol) in toluene is azeotropically dried using a Dean-Stark trap to obtain the anhydrous acid. Toluene is then removed in vacuo and replaced with propionitrile. The resultant solution is treated with N-(p-chloro-α-cyanobenzyl)-2,2,2-trifluoroacetamide (13.1 g, 0.05 mol) and 2-chloroacrylonitrile (8.75 g, 0.1 mol), heated at 98°–100° C. for 18 hours, cooled to room temperature and quenched with a mixture of water and ethyl acetate. The phases are separated and the organic phase is washed with water and concentrated in vacuo to give a residue. Flash column chromatography of the residue using silica gel packed and eluted with 20% ethyl acetate in heptane gives the title product as pale yellow crystals, 4.2 g (39% yield), identified by HPLC and NMR analyses.

EXAMPLE 7

Preparation of Methyl 2-(p-chlorophenyl)-5-(trifluoromethyl)-pyrrole-3-carboxylate

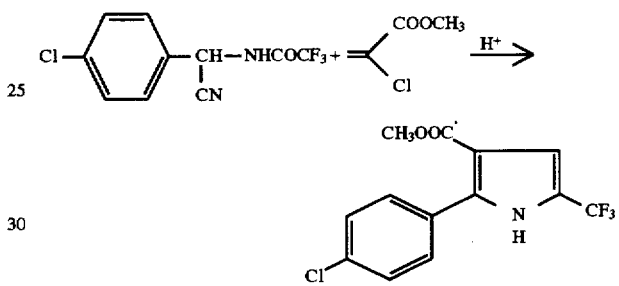

A slurry of N-(p-chloro-α-cyanobenzyl)-2,2,2-trifluoroacetamide (10.5 g, 0.04 mol) in toluene under a nitrogen atmosphere is cooled to 10° C., treated with trifluoromethanesulfonic acid (12.0 g, 0.08 mol) over 10–15 minutes, allowed to warm to room temperature and stirred for 3 hours. The reaction is monitored by $^{19}$F NMR (DMSO-$d_6$) analysis to show completion of the intermediate salt formation. When formation is complete, the mixture is cooled to 10° C., treated with dimethylformamide, treated with methyl 2-chloroacrylate (7.2 g, 0.06 mol), allowed to warm to room temperature, stirred for 18 hours, and diluted with water and ethyl acetate. The phases are separated and the organic phase is washed with water and concentrated to give a waxy solid residue. Flash column chromatography of the residue on silica gel, packed and eluted with 20% ethyl acetate in heptane gives the title product as a white crystalline solid, 7.6 g (62% yield), mp 123°–125° C. identified by $^1$H and $^{19}$F NMR analyses.

Example 8

Preparation of 2-(p-Chlorophenyl)-1-methyl-5-(trifluoromethyl) pyrrole-3-carbonitrile

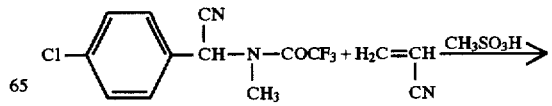

-continued

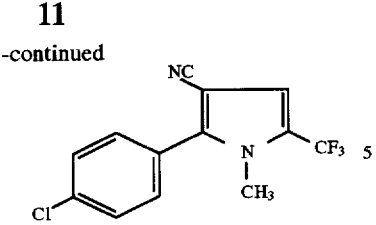

A solution of N-(p-chloro-α-cyanobenzyl-2,2,2-trifluoro-N-methylacetamide (13.8 g, 0.05 mol) in toluene is treated with acrylonitrile (5.3 g, 0.1 mol) and methanesulfonic acid (9.6 g, 0.1 mol), heated at 108°–110° C. for 30 hours, quenched with water and extracted with ethyl acetate. The organic extracts are combined and concentrated in vacuo to give a residue. The residue is purified by flash column chromatography on silica gel, packed and eluted with 15% ethyl acetate in heptane to give the title product as a pale yellow solid, 0.9 g (63% yield), mp 129°–130° C., identified by $^1$H and $^{19}$F NMR analyses.

EXAMPLE 9

Preparation of 2-(p-Chlorophenyl)-1-methyl-5-(trifluoromethyl) pyrrole-3-carbonitrile

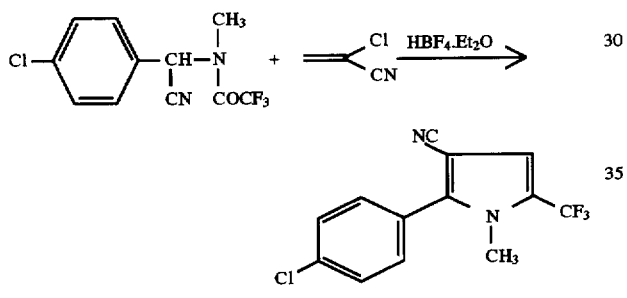

A solution of N-(p-chloro-α-cyanobenzyl)-2,2,2-trifluoro-N-methylacetamide (13.8 g, 0.05 mol) in toluene is treated with tetrafluoroboric acid-diethyl etherate (10.5 g as is, 8.9 g real, 0.055 mol) at room temperature, heated to 60° C., treated with 2-chloroacrylonitrile (6.9 g, 0.075 mol) over a 25 minute period, held for 2 to 2.5 hours at 60° C., cooled and treated with ethyl acetate. The resultant solution is washed with water and concentrated to give a waxy residue. Flash column chromatography of the residue on silica gel packed with 15% ethyl acetate in heptane and eluted with 20% ethyl acetate in heptane gives the title product as pale yellow crystals, 3.1 g (22% yield), mp 129°–130° C., identified by $^1$H, $^{13}$C, and $^{19}$F NMR analyses.

EXAMPLE 10

Preparation of 2-(p-Chlorophenyl)-1-methyl-5-(trifluoromethyl) pyrrole-3-carbonitrile

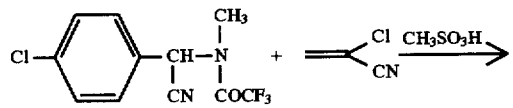

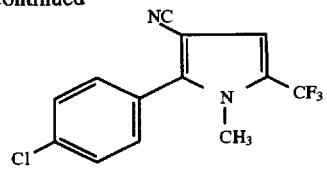

A solution of N-(p-chloro-a-cyanobenzyl)-2,2,2-trifluoro-N-methylacetamide (13.8 g, 0.05 mol) in toluene is treated with 2-chloroacrylonitrile (4.4 g, 0.05 mol) and methanesulfonic acid (4.8 g, 0.05 mol), heated at 110° C. for 4 hours, treated with a second portion of 2-chloroacrylonitrile (4.4 g, 0.05 mol) and methanesulfonic acid (4.8 g, 0.05 mol), heated at 110° C. for 12 hours, cooled and treated with ethyl acetate and water. The phases are separated and the organic phase is washed with water and concentrated to give a residue. The residue is chromatographed using silica gel packed with 15% ethyl acetate in heptane and eluted with 20% ethyl acetate in heptane to give the title product as pale yellow crystals, 4.8 g (34% yield), mp 129°–130° C.

EXAMPLE 11

Preparation of 2-(p-Chlorophenyl)-1-isopropyl-5-(trifluoromethyl) pyrrole-3-carbonitrile

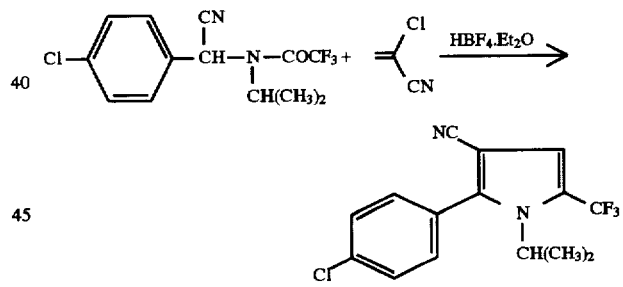

A solution of N-(p-chloro-α-cyanobenzyl)-2,2,2-trifluoro-N-isopropylacetamide (6.1 g, 0.02 mol) in toluene is treated at room temperature with tetrafluoroboric acid diethyl etherate (4.2 g as is, 3.6 g real, 0.022 mol) under a nitrogen atmosphere, heated to 60° C., treated with 2-chloroacrylonitrile (2.62 g, 0.03 mol) over 15–20 minutes, held at 60° C. for 3 hours, cooled to room temperature and treated with ethyl acetate and water. The phases are separated and the organic phase is washed with water and concentrated to give a brown gum residue. Flash column chromatography of the residue on silica gel packed and eluted with 15% ethyl acetate in heptane gives the title product as a brown oil, 1.3 g (20.8% yield), identified by $^1$H and $^{19}$F NMR and mass spectral analyses.

EXAMPLE 12

Preparation of 1-Benzyl-2-(p-chlorophenyl)-5-(trifluoromethyl) pyrrole-3-carbonitrile

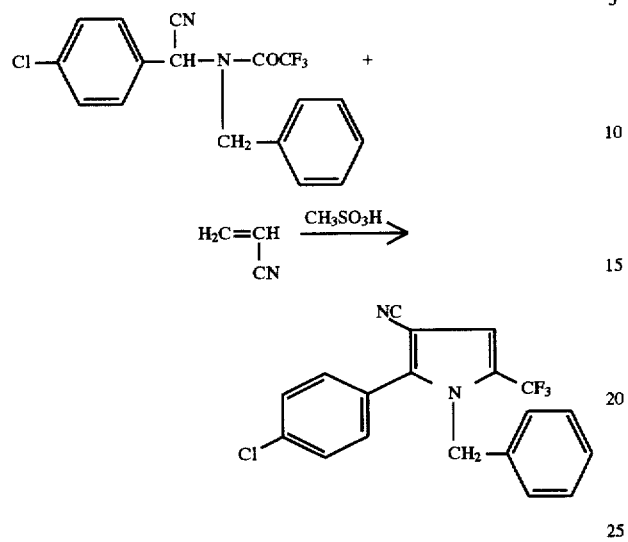

A solution of N-(p-chloro-α-cyanobenzyl)-2,2,2-trifluoro-N-benzylacetamide (10.6 g, 0.03 mol) in toluene is treated with methanesulfonic acid (3.2 g, 0.033 mol) and acrylonitrile (3.9 g, 0.045 mol), heated at 100°–105° C. for 18 hours, cooled, treated with additional methanesulfonic acid (1.6 g, 0.017 mol), heated at 100°–105° C. for 22 hours, quenched with water and extracted with ethyl acetate. The organic extracts are combined and concentrated in vacuo to give a residue. The residue is purified by flash column chromatography using silica gel packed and eluted with 15% ethyl acetate in heptane to give the title product as white crystals, 4.4 g (40.6% yield), mp 103.5°–105.5° C., identified by $^1$H, $^{13}$C and $^{19}$F NMR and mass spectral analyses.

I claim:

1. A process for making a compound of formula IV

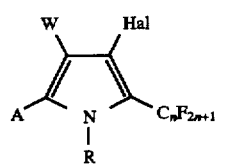 (IV)

wherein R is hydrogen or $C_1$–$C_6$alkyl optionally substituted with one $C_1$–$C_4$alkoxy or phenyl group;

n is an integer of 1, 2, 3, 4, 5, 6, 7 or 8;

W is CN, $NO_2$, $COOR_1$, or $COR_2$;

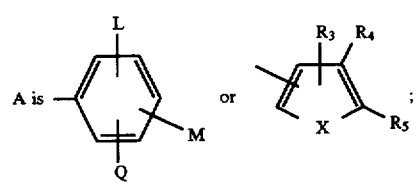

L is hydrogen or halogen;

M and Q are each independently hydrogen, halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$alkylsulfinyl or when M and Q are on adjacent positions they may be taken together with the carbon atoms to which they are attached to form a ring in which MQ represents the structure —$OCH_2O$—, —$OCF_2O$— or —CH=CH—CH=CH—;

$R_1$ and $R_2$ are each independently $C_1$–$C_4$alkyl;

$R_3$, $R_4$, and $R_5$ are each independently hydrogen, halogen, $NO_2$, CHO or $R_4$ and $R_5$ may be taken together with the atoms to which they are attached to form a ring in which $R_4R_5$ is represented by the structure

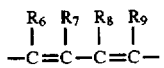

$R_6$, $R_7$, $R_8$ and $R_9$ are each independently hydrogen, halogen, CN or $NO_2$;

X is O or S; and

Hal is a halogen atom; which comprises reacting an amide nitrile of formula II

 (II)

wherein A, R and n are as described hereinabove for formula I with at least one molar equivalent of a dieneophile of formula III

 (III)

wherein W is as described hereinabove for formula I and Y is hydrogen, Br or Cl with the proviso that when R is hydrogen, then Y must be Br or Cl, in the presence of an acid and a solvent and essentially in the absence of water to form a formula I compound

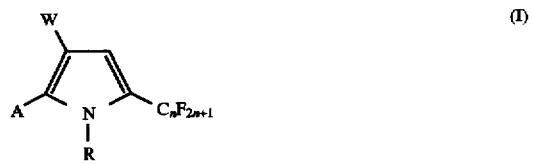 (I)

and halogenating said formula I compound to form said formula IV compound.

2. A compound of formula IIa

 (IIa)

wherein n is an integer of 1, 2, 3, 4, 5, 6, 7 or 8;

R' is $C_1$–$C_6$alkyl optionally substituted with one $C_1$–$C_4$alkoxy or phenyl group;

A is 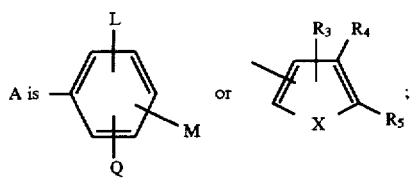

L is hydrogen or halogen;

M and Q are each independently hydrogen, halogen, CN, $NO_2$, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfinyl or when M and Q are on adjacent positions they may be taken together with the carbon atoms to which they are attached to form a ring in which MQ represents the structure —$OCH_2O$—, —$OCF_2O$— or —CH=CH—CH=CH—;

$R_1$ and $R_2$ are each independently $C_1$-$C_4$alkyl;

$R_3$, $R_4$, and $R_5$ are each independently hydrogen, halogen, $NO_2$, CHO or $R_4$ and $R_5$ may be taken together with the atoms to which they are attached to form a ring in which $R_4R_5$ is represented by the structure

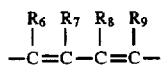

$R_6$, $R_7$, $R_8$ and $R_9$ are each independently hydrogen, halogen, CN or $NO_2$; and X is O or S.

3. The compound according to claim 2 wherein n is 1 or 2.

4. The compound according to claim 2 wherein R' is methyl or ethoxymethyl.

5. The compound according to claim 2 wherein A is

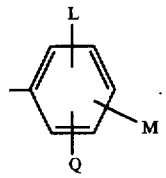

6. The compound according to claim 5 wherein L is hydrogen or halogen and M and Q are each independently hydrogen, halogen or $C_1$-$C_4$haloalkyl.

7. The compound according to claim 6 wherein n is 1 and R' is methyl.

8. The compound according to claim 3 N-(p-chloro-α-cyanobenzyl)-2,2,2-trifluoro-N-methylacetamide.

9. The compound according to claim 3 N-(p-chloro-α-cyanobenzyl)-2,2,2-trifluoro-N-isopropylacetamide.

10. The compound according to claim 3 N-(3,5-dichloro-α-cyanobenzyl)-2,2,2-trifluoro-N-methylacetamide.

11. The compound according to claim 3 N-(p-chloro-α-cyanobenzyl)-2,2,2-trifluoro-N-benzylacetamide.

\* \* \* \* \*